United States Patent
Gavrilovic

[19]

[11] 3,951,846
[45] Apr. 20, 1976

[54] NOVEL LIQUID CRYSTAL ELECTRO-OPTIC DEVICES

[75] Inventor: Dragan Milan Gavrilovic, Cranbury, N.J.

[73] Assignee: RCA Corporation, New York, N.Y.

[22] Filed: June 28, 1974

[21] Appl. No.: 484,087

[52] U.S. Cl............................. 252/299; 252/408; 260/463; 260/465 D; 260/465 F; 260/465 R; 350/160 LC
[51] Int. Cl.[2]...................... C09K 3/34; G02F 1/13; C07C 121/64; C07C 69/96
[58] Field of Search..................... 252/299, 408 LC; 350/160 LC; 260/465 D, 465 F, 465 R, 463

[56] References Cited
UNITED STATES PATENTS

| | | | |
|---|---|---|---|
| 3,795,436 | 3/1974 | Boller et al. | 252/408 LC |
| 3,796,479 | 3/1974 | Helfrich et al. | 252/408 LC |

FOREIGN PATENTS OR APPLICATIONS

| | | | |
|---|---|---|---|
| 807,165 | 3/1974 | Belgium | 252/299 |
| 2,327,036 | 12/1973 | Germany | 252/299 |
| 2,306,739 | 8/1973 | Germany | 252/299 |

OTHER PUBLICATIONS
Gray, G. W. et al., Liquid Crystals & Plastic Crystals, Vol. 1, Ellis Horwood, Ltd.; London, pp. 103–152 (1/74).
Usol'tseva, V. A. et al., Russian Chem. Rev., Vol. 32, No. 9, pp. 495–507, (Sept., 1963).

*Primary Examiner*—Benjamin R. Padgett
*Assistant Examiner*—T. S. Gron
*Attorney, Agent, or Firm*—Glenn H. Bruestle; Birgit E. Morris

[57] ABSTRACT

Nematic liquid crystal compounds of the formula:

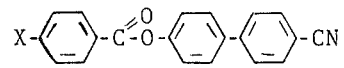

wherein X can be hydrogen, alkyl (R-), alkoxy (RO-), acyloxy

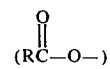

or alkylcarbonato

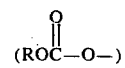

wherein R is an alkyl group of 1–10 carbon atoms, have positive dielectric anisotropy and are useful in electro-optic cells which comprise a thin liquid crystal layer between two closely spaced parallel electrodes.

9 Claims, 1 Drawing Figure

U.S. Patent  April 20, 1976  3,951,846
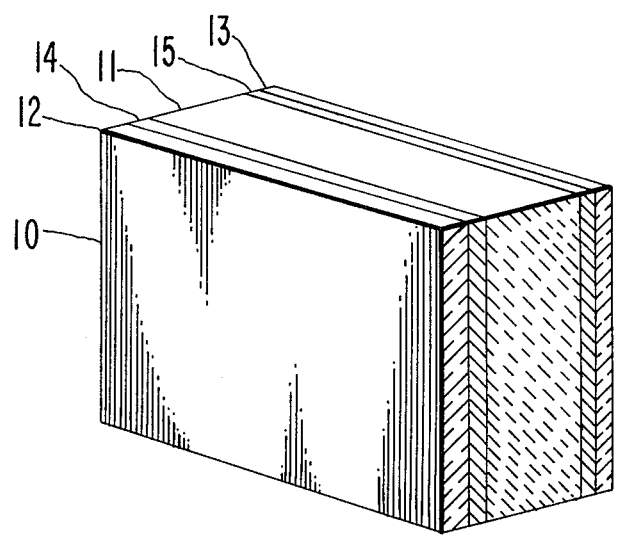

1

NOVEL LIQUID CRYSTAL ELECTRO-OPTIC DEVICES

This invention relates to novel liquid crystal compounds and to electro-optic devices including them. More particularly, this invention relates to nematic liquid crystal compounds having positive dielectric anisotropy and to field effect liquid crystal cells.

BACKGROUND OF THE INVENTION

Mesomorphic or liquid crystal compounds are of increasing interest in a variety of electro-optic display devices. Nematic liquid crystals are of particular interest for electrically controllable, flat panel displays such as watch faces, digital clocks, calculator displays, numeric displays for instruments and the like. Typically, a liquid crystal cell comprises a thin layer of a liquid crystal composition sandwiched between two closely spaced parallel conductive plates, at least one of which is transparent. When the conductive plates are connected to a source of current, an electric field is generated in the liquid crystal composition.

Nematic liquid crystal cells can operate in a dynamic scattering mode, as is described in U.S. Pat. No. 3,499,112 to Heilmeier and Zanoni, or in a field effect mode. Field effect devices contain nematic compounds or mixtures of compounds having positive dielectric anisotropy, that is, the magnitude of the dielectric constant in a direction parallel to the long axis of the molecular chain is greater than the magnitude of the dielectric constant in a direction perpendicular to the long axis of the molecular chain, between conductive plates that have been treated so that the liquid crystal molecules align themselves in a particular direction, usuallly parallel, to the plane of the plates. When an electric field is applied, the positive dielectric anisotropy of the molecules causes the molecules to realign themselves in a direction parallel to the applied field and perpendicular to the plates. The change in alignment is made visible using a polarizer and an analyzer on either side of the cell. Field effect liquid crystal cells have the advantages of lower threshold voltages and wider viewing angle than dynamic scattering cells and have excellent contrast and long lifetimes.

Each mesomorphic compound has a particular temperature range in which it is an ordered liquid, ranging from the solid to nematic liquid crystal melting point up to the temperature at which it forms an isotropic liquid. This is the temperature range useful in electro-optic cells. Although, as is known, wide variations in use temperature can be effected by employing mixtures of liquid crystal compounds that are compatible with each other, no single liquid crystal compound or mixture of compounds can satisfy all use temperature ranges desired. Thus, new liquid crystal compounds which have different use temperature ranges are being sought to satisfy various temperature requirements for which the liquid crystal cells will be employed.

SUMMARY OF THE INVENTION

It has been discovered that certain nematic liquid crystal compounds derived from 4-cyano-4'-hydroxybiphenyl which have positive dielectric anisotropy and have a very broad mesomorphic temperature range are useful in flat panel electro-optic devices.

BRIEF DESCRIPTION OF THE DRAWING

The FIGURE is a cross-sectional view of an electro-optic device embodying the invention.

DETAILED DESCRIPTION OF THE INVENTION

The novel liquid crystal compounds have the formula:

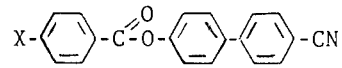

wherein X can be hydrogen, R—, RO—,

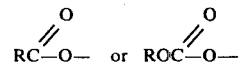

wherein R is an alkyl group of 1–10 carbon atoms. Thus X can be hydrogen, an alkyl group, an alkoxy group, an acyloxy group or an alkylcarbonato group respectively. Both branched and straight chain alkyl groups are included but at the present time straight chain alkyl groups are preferred. These compounds are stable nematic compounds have high and very broad mesomorphic temperature ranges. They can be employed in electro-optic devices alone, in admixture with each other or in admixture with other liquid crystal compounds to broaden the use temperature range or vary the response of the cell.

The present compounds can be prepared by reacting 4-cyano-4'-hydroxybiphenyl with a benzoyl chloride. The nematic liquid crystal compound can be purified by conventional means, as by recrystallization, fractional distillation, or chromatography.

Referring to the FIGURE, a liquid crystal cell 10 comprises a layer of a liquid crystal composition 11 between a front transparent support plate 12 and a back support plate 13. The front support plate 12 is coated on the inside with a transparent conductive layer 14 to form an electrode. The back support plate 13 is also provided on the inside with a conductive layer 15 to form the other electrode. If light is to be transmitted through the cell, the back electrode 15 and the back support plate 13 are also transparent. If the liquid crystal cell is to reflect light, the back electrode 15 can be made reflective. As is known, additional compounds such as wetting agents, aligning agents and the like can be added to the liquid crystal composition to improve the optical or electrical performance of the cell. The electro-optic devices described above can be incorporated into various displays, such as electronic clocks, watches, advertising displays, numeric indicators and the like.

The invention will be further illustrated by the following examples but it is to be understood that the invention is not meant to be limited to the details described therein. In the examples, parts and percentages are by weight unless otherwise noted.

The transition temperatures of the compounds prepared in the examples were determined using a Thomas-Hoover melting point apparatus, a differential scanning calorimeter and a polarizing hot stage microscope in conventional manner.

EXAMPLE 1

Preparation of p-n-hexylcarbonato-p'-(4-cyano-4'-biphenyl)benzoate

PART A

Preparation of p-n-hexylcarbonatobenzoic acid

Eighty parts of sodium hydroxide was dissolved in 2000 parts of water and cooled below 10°C. P-n-hydroxybenzoic acid (138.1 parts) was dissolved in the sodium hydroxide solution and n-hexylchloroformate (164.6 parts) was added dropwise over a half hour period while stirring. Stirring was continued at 5°–10°C. for one hour and the resultant mixture extracted with 500 parts by volume of ether. An excess of 18 percent hydrochloric acid (200 parts by volume) was stirred into the aqueous solution to precipitate the product. The product was filtered and washed with water. It was then dissolved in 1500 parts by volume of ether, dried with anhydrous sodium sulfate, filtered and the solvent evaporated.

The resultant product (239 parts) of p-n-hexylcarbonatobenzoic acid had a melting point of 120°–126°C.

PART B

Preparation of p-n-hexylcarbonatobenzoyl chloride

The product as prepared in Part A, 300 parts by volume of benzene and 150 parts by volume of thionyl chloride were charged to a vessel equipped with a magnetic stirrer and a reflux condenser having a drying tube thereon. The mixture was stirred and refluxed for five hours. The solvent was then evaporated under vacuum and the product redistilled twice at 140°–142°/0.08 mm. The product was obtained in 81.8 percent yield (209.7 parts).

PART C

Preparation of 4-cyano-4'-hydroxybiphenyl

A reaction mixture of 23.3 parts of 4-bromo-4'-hydroxybiphenyl, 11.2 parts of cuprous chloride and 60 parts by volume of dimethylformamide was charged to a vessel equipped with a magnetic stirrer and a reflux condenser with a drying tube. The mixture was refluxed for 24 hours and poured over 500 parts of an aqueous solution containing 50 parts by volume of concentrated hydrochloric acid and 50 parts of ferric chloride. The mixture was stirred at about 60°C. for 2 hours, cooled to room temperature and extracted three times with 300 parts by volume portions of ether. The combined ether extracts were washed three times with 500 parts of water, dried over anhydrous sodium sulfate and the solvent evaporated. The product was recyrstallized from 200 parts by volume of a 2:1:1 mixture of acetone-hexane-chloroform.

Ten parts (51 percent yield) of 4-cyano-4'-hydroxybiphenyl were obtained having a melting point of 193°–195°C.

PART D

Preparation of p-n-hexylcarbonato-p'-(4-cyano-4'-biphenyl)benzoate

A reaction mixture of 2.8 parts of p-n-hexylcarbonatobenzoyl chloride as prepared in Part B, 50 parts by volume of benzene, 1.9 parts of 4-cyano-4'-hydroxybiphenyl and 5 parts by volume of pyridine was charged to a vessel equipped with a stirrer and a reflux condenser. The mixture was refluxed for one hour and stirred at room temperature overnight. The precipitate was removed by filtration. The filtrate was washed with 50 part portions of dilute (3.5 percent) hydrochloric acid three times and with 50 parts of saturated sodium chloride solution. The organic layer was separated, dried over anhydrous sodium sulfate and the solvent evaporated. The product was recrystallized once from 1500 parts by volume of hexane and once from 100 parts by volume of ethyl acetate.

P-n-hexylcarbonato-p'-(4-cyano-4'-biphenyl)benzoate having the formula:

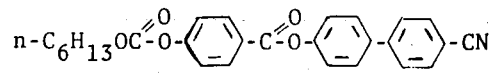

was obtained in 50 percent yield (2.25 parts) as a white solid. The product had a crystal to nematic liquid transition temperature of 108°–108.5°C. and a nematic to isotropic liquid transition temperature of 238°C.

The structure was confirmed by infrared analysis which showed cyano group absorption at 2248 cm$^{-1}$ and carbonyl group absorptions at 1760 and 1735 cm$^{-1}$; and by elemental analysis. Theoretical: C, 73.12%; H, 5.68%; N, 3.16%. Found: C, 73.67%; H, 5.77%; N, 3.13%. A thin layer chromatogram developed with 9:1 hexane-tetrahydrofuran showed only one compound was present.

EXAMPLE 2

Preparation of p-n-butylcarbonato-p'-(4-cyano-4'-biphenyl)benzoate

Following the general procedure of Example 1 except substituting n-butylchloroformate for the n-hexylchloroformate, p-n-butylcarbonato-p'-(4-cyano-4'-biphenyl)benzoate having the formula:

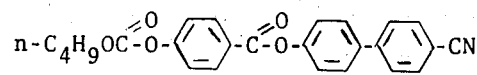

was obtained. This compound had a crystal to nemataic liquid transition temperature of 109°–110°C. and a nematic to isotropic liquid transition temperature of 262°C.

EXAMPLE 3

Preparation of p-n-pentylcarbonato-p'-(4-cyano-4'-biphenyl)benzoate

Following the general procedure of Example 1 except substituting n-pentylchloroformate for the n-hexylchloroformate, p-n-pentylcarbonato-p'-(4-cyano-4'-biphenyl)benzoate having the formula:

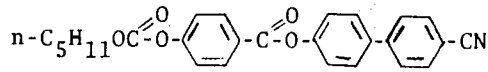

was obtained. This compound had a crystal to nematic liquid transition temperature of 109°–110°C. and a nematic to isotropic liqiuid transition temperature of 248°C.

EXAMPLE 4

Preparation of p-n-hexanoyloxy-p'-(4-cyano-4'-biphenyl)benzoate

PART A

Preparation of p-n-hexanoyloxybenzoic acid

A reaction mixture of 19.0 parts of p-hydroxybenzoic acid, 42.8 parts of n-hexanoic anhydride, 15 parts by volume of benzene and one part by volume of sulfuric acid was charged to a vessel equipped with a magnetic stirrer and a reflux condenser. The reaction mixture was refluxed while stirring for 15 minutes, and poured into 300 parts of an ice-water mixture. The mixture was extracted with 300 parts by volume of methylene chloride, the organic extract dried over anhydrous sodium sulfate, filtered and the solvent evaporated. The resultant product was recrystallized from 700 parts by volume of hexane.

The product was a monotropic liquid crystal compound having a crystal to isotropic liquid melting point of 152°–153°C. and an isotropic to nematic liquid transition temperature of 138°C.

PART B

Preparation of p-n-hexanoyloxybenzoyl chloride

This compound was prepared following the general procedure of Example 1 Part B except substituting the compound of Part A above the the p-n-hexylcarbonatobenzoic acid. The product was purified by distilling at 125°C/0.1 mm.

PART C

Preparation of p-n-hexanoyloxy-p'-(4-cyano-4'-biphenyl)benzoate

Following the general procedure of Example 1 Part D except substituting p-n-hexanoyloxybenzoyl chloride for the p-n-hexylcarbonatobenzoyl chloride, p-n-hexanoyloxy-p'-(4-cyano-4'-biphenyl)benzoate was obtained having the formula:

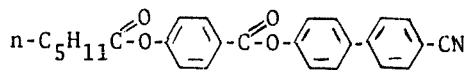

This compound had a crystal to smectic liquid transition temperature of 86°C., a smectic to nematic liquid transition temperature of 91°C. and a nematic to isotropic liquid transition temperature of 262.5°C.

EXAMPLE 5

Preparation of 4-cyano-4'-biphenylbenzoate

Following the general procedure of Example 1 Part D except substituting benzoyl chloride for the p-n-hexylcarbonatobenzoyl chloride, the compound

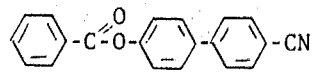

was prepared. This compound is a monotropic liquid crystal compound having a crystal to isotropic liquid melting point of 210°–213°C. Upon cooling, it exhibited an isotropic to nematic liquid transition temperature of 197.5°C.

EXAMPLES 6–12

Following the general procedure of Example 1 Part D, but substituting the appropriate p-alkyl and p-alkoxy substituted-benzoyl chloride compounds for the p-n-hexylcarbonatobenzoyl chloride, additional liquid crystal compounds were prepared. The following Table summarizes the alkyl or alkoxy substituent and the transition temperatures, wherein C-N is the crystal to nematic liquid transition temperature and N-L is the nematic to isotropic liquid transition temperature.

TABLE

| Example | Alkyl or Alkoxy Substituent | C-N, °C. | N-L, °C. |
|---|---|---|---|
| 6 | $CH_3-$ | 193–195 | 279–279.5 |
| 7 | $C_3H_7-$ | 113–114 | 258.5–259 |
| 8 | $C_5H_{11}-$ | 106–107 | 239 |
| 9 | $C_6H_{13}-$ | 91–92 | 226.5 |
| 10 | $C_4H_9O-$ | 116–117 | 272 |
| 11 | $C_7H_{15}O-$ | 93–94 | 240.5 |
| 12 | $C_8H_{17}O-$ | 95.5–96 | 234 |

EXAMPLE 13

Preparation of p-n-decyl-p'-(4-cyano-4'-biphenyl)benzoate

Following the general procedure of Example 1 Part D except substituting p-n-decylbenzoyl chloride for the p-n-hexylcarbonatobenzoyl chloride, p-n-decyl-p'-(4-cyano-4'-biphenyl)benzoate was prepared having the formula:

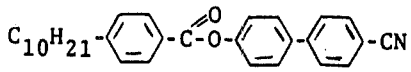

This compound had a crystal to smectic liquid transition temperature of 89°C., a smectic to nematic liquid transition temperature of 198°C. and a nematic to isotropic liquid transition temperature of 202°C.

I claim:

1. In an electro-optic cell comprising a liquid crystal layer between two electrodes, the improvement which comprises including in the liquid crystal layer a compound of the formula

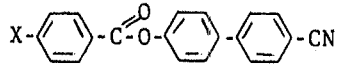

wherein X is a member selected from the group consisting of hydrogen, R—, RO—,

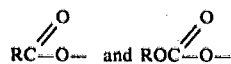

groups wherein R is an alkyl group of 1–10 carbon atoms.

2. The device according to claim 1 wherein both electrodes are transparent.

3. A liquid crystal compound having the formula:

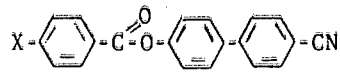

wherein X is a member selected from the group consisting of hydrogen, R—, RO—,

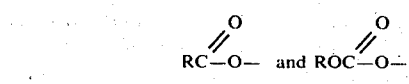 groups wherein R is an alkyl group of 1–10 carbon atoms.

4. A compound according to claim 3 wherein X is hydrogen.

5. A compound according to claim 3 wherein X is an R group.

6. A compound according to claim 3 wherein X is an RO group.

7. A compound according to claim 3 wherein X is an

group.

8. A compound according to claim 3 wherein X is an

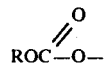

group.

9. A compound according to claim 3 wherein R is a straight chain alkyl group.

* * * * *